United States Patent [19]
Cummings et al.

[11] Patent Number: 5,593,439
[45] Date of Patent: Jan. 14, 1997

[54] VOCAL CORD LATERALIZATION AND MEDIALIZATION DEVICE AND METHOD

[75] Inventors: Charles W. Cummings; Paul W. Flint; Peter J. Scranton, all of Baltimore, Md.

[73] Assignee: Johns Hopkins University, Baltimore, Md.

[21] Appl. No.: 446,315

[22] Filed: May 22, 1995

[51] Int. Cl.⁶ .................................................. A61F 2/20
[52] U.S. Cl. ................................................ 623/9; 623/11
[58] Field of Search ............................................ 623/9, 11

[56] References Cited

U.S. PATENT DOCUMENTS

| | | | |
|---|---|---|---|
| 5,201,765 | 4/1993 | Netterville et al. | 623/9 |
| 5,306,298 | 4/1994 | Godley, III et al. | 623/9 |
| 5,326,375 | 7/1994 | Montgomery et al. | 623/11 |
| 5,391,205 | 2/1995 | Knight | 623/9 |

FOREIGN PATENT DOCUMENTS 0551198  7/1993  European Pat. Off. ............... 623/9

*Primary Examiner*—John G. Weiss
*Assistant Examiner*—Francis K. Cuddihy
*Attorney, Agent, or Firm*—Cushman Darby & Cushman IP Group of Pillsbury Madison & Sutro, LLP

[57] ABSTRACT

A device and method to lateralize, or alternatively medialize, the vocal cord is described that is adjustable so that the final position of the vocal cord can be adjusted to enhance the quality of the patient's voice following the procedure. The multi-component device preferably includes, in the case of lateralization, a collar, a translation bushing, and a piston having a grasping device which is inserted through the thyroid cartilage and activated to grasp the vocalis process region of the arytenoid cartilage and lateralize the arytenoid. In the case of medialization, the multi-component device includes a collar and a bushing mounted for displacement relative to the collar, toward the targeted process, to push the process and/or engage a push-plate to medialize the process.

22 Claims, 1 Drawing Sheet

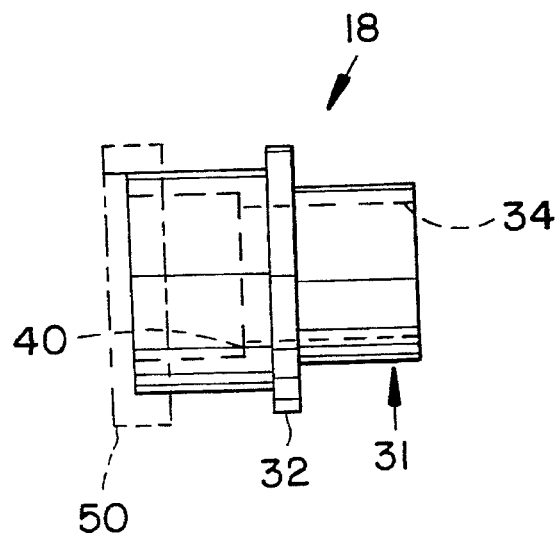
FIG. 1
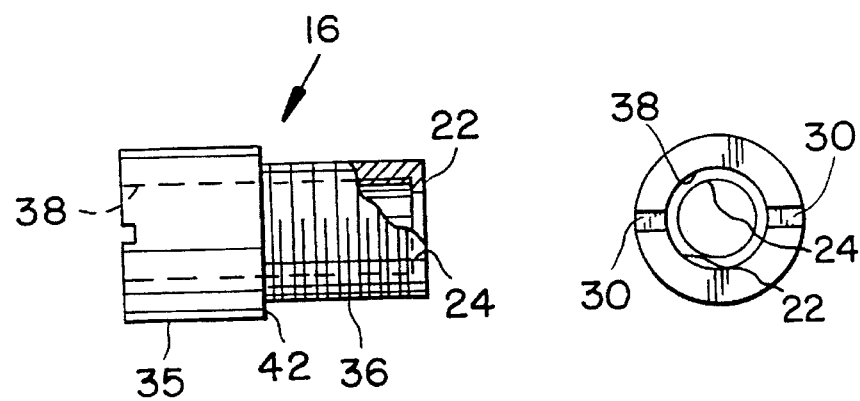
FIG. 2
FIG. 3
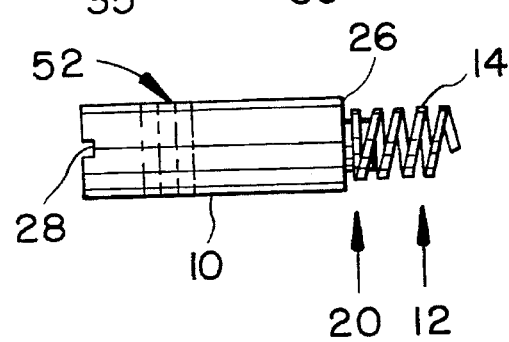
FIG. 4

VOCAL CORD LATERALIZATION AND MEDIALIZATION DEVICE AND METHOD

BACKGROUND OF THE INVENTION

1. Field of the Invention

The present invention relates to a method and device to achieve vocal cord lateralization or medialization, as indicated, during surgery. More particularly, the invention provides a method and device for tunable or adjustable lateralization of the vocal cord in patients who have bilateral limitation in abduction on the basis of a neurological deficit or pathology centering on the cricoarytenoid joint.

2. Description of the Related Art

Current procedures for correcting the deficit of a compromised airway, which is the significant sequelae to bilateral abductor paralysis, involves surgical removal of the arytenoid cartilage either through an operating laryngoscope or via an external approach through the neck. The laser has been used as a tool for removing the cartilage and recently has been used to divide the vocal cord horizontal to the long axis of the cord which creates a better airway, but with substantial sacrifice to the quality of the patient's voice.

Procedures have been proposed to displace the vocal cord to a more lateralized position to improve the quality of airway. For example, there are procedures wherein a suture is used which traverses the thyroid cartilage, extends to or travels through the arytenoid cartilage, and back out. Traction laterally will pull or tether the vocal cord in a more lateralized position. However, such procedures create a very variable end result and do not have the advantage of being reversible and/or tunable.

SUMMARY OF THE INVENTION

It is an object of the present invention to provide a device and method to lateralize, or alternatively medialize, the vocal cord, that is effectively infinitely adjustable so that the final position of the vocal cord can be adjusted to enhance the quality of the patient's voice and airway following the procedure.

The foregoing and other objects of the invention are achieved by providing a multi-component device including, in the case of lateralization, a collar and a piston having a grasping device which is inserted through the thyroid cartilage and activated to grasp the vocalis process region of the arytenoid cartilage and lateralize the arytenoid. In the currently preferred embodiment, a translation bushing is incorporated intermediate the collar and the piston. In the case of medialization, the objects of the invention are achieved by providing a multi-component device including a collar and a bushing mounted for displacement relative to the collar, toward the targeted process, to push the process and/or engage a push-plate to medialize the process.

Thus, in accordance with the invention, a window is made in the thyroid cartilage at the same vertical level as the vocal cord and the arytenoid cartilage. A collar component is inserted into this window. Subsequently, a piston is introduced directly, or indirectly via the translation bushing of the preferred embodiment, through the lumen of the collar. At the distal end of the piston, a grasping device is provided which is activated through adjustment at the proximal or outermost end of the prosthesis. The vocalis process region of the arytenoid cartilage is grasped by the grasping device and then the piston is displaced axially relative to the collar to lateralize the arytenoid to a point where the airway is improved and the voice minimally impaired.

The foregoing procedure may be accomplished under local anesthesia with basal-sedation in the same fashion as with known medialization procedures.

Other objects, features, and characteristics of the present invention as well as the methods of operation and functions of the related elements of structure, and the combination of parts and economies of manufacture, will become more apparent upon consideration of the following description and the appended claims with reference to the accompanying drawings, all of which form a part of this specification, wherein like reference numerals designate corresponding parts in the various figures.

BRIEF DESCRIPTION OF THE DRAWINGS

FIG. 1 is a schematic elevational view of an anchor flange collar provided in accordance with the invention;

FIG. 2 is a schematic elevational view of a translation bushing provided in accordance with the invention with a distal portion thereof broken away to show exemplary details of the invention;

FIG.3 is an end view of the translation bushing taken from the left of FIG. 2; and FIG. 4 is a schematic elevational view of a preferred coil rod assembly provided in accordance with the invention.

DETAILED DESCRIPTION OF THE PRESENTLY PREFERRED EXEMPLARY EMBODIMENT

As described above, it is an object of the present invention to provide a method for lateralization, as a primary function, and medialization, as an alternative function, of the vocal cord by manipulating the adjacent arytenoid process. The method can be effected by direct engagement with the cartilage and/or the soft tissue attached to the cartilage. As will become apparent from the detailed description to follow, the device is adapted to provide incremental (infinitely adjustable) translational motion, which allows the vocal cord to be tuned to the proper level of phonation. Moreover, the device is adapted for easy removal although it is not contemplated that the functional service life of the implant is restricted.

The currently most preferred embodiment of the invention is comprised of four components. The first, centrally located component is a rod 10, which may be formed from Cobalt-Chrome or Titanium. The second component, a grasping device 12, is provided at the distal end of the rod. In the illustrated embodiment, the grasping device is a coil 14, preferably a Cobalt-Chrome wire, the function of which will be described more particularly below. The third component in the illustrated embodiment is a translation bushing 16 which is adapted to axially shift the rod 10. The translation bushing 16 may be formed, for example, from Cobalt-Chrome, stainless steel, or Titanium. The fourth component, an anchor flange 18 which may, for example, be formed from ultrahigh molecular weight polyethylene (UHMWPE) receives the translation bushing 16.

In practice, the plastic anchor flange 18 is placed within the cartilage of the thyroid process which is located anteriorly with respect to the arytenoid process. Threaded within the plastic anchor flange 18 is the translation bushing 16 which provides both alignment for the coil-rod assembly 20, which is in use inserted into the tissue adjacent to the arytenoid process, and axial motion (lateralization) for the coil-rod assembly 20 upon activation.

As shown in FIG. 4, the coil-rod assembly 20 is comprised of the small rod 10 with the "corkscrew" or helix type coil structure 14 mounted at the tip thereof. The coil-rod is inserted through the translation bushing 16, after placement of the anchor flange, and is rotated in a counterclockwise direction as contact is made with the connective tissue of the arytenoid process. In the illustrated embodiment, the tissue is engaged by the helical coil as a result of the counterclockwise rotation of the coil-rod assembly.

Displacement of the coil-rod 20 axially, distally relative to the bushing 16 is limited, in the illustrated embodiment, by the provision of a radially inwardly directed flange 22 at the distal end of the translation bushing 16. The flange 22 defines a distal opening 24 large enough for the coil 14 or other grasping device 12 to pass but too small for the rod 10 to pass. Following the engagement of the tissue, the translation bushing 16 is turned counterclockwise. Engagement of the radial flange 22 of the translation bushing 16 with the distal end 26 of the rod 10 or a shoulder otherwise defined at a particular point along the length of the rod, causes the coil-rod assembly 20 to move axially backward (or laterally).

A key aspect of the function between the device components is the coil-rod's axial motion, free of rotation. The translation bushing 16, since it is threaded into the plastic flange 18, moves axially as it is unthreaded. The bushing rotates about the coil-rod assembly 20 which is engaged by the tissue. The coil-rod assembly 20 is pulled laterally without rotation. Rotational movement of the coil-rod would be undesirable since engagement of the tissue with the coil may be compromised. However, because counterclockwise rotation of the coil-rod furthers engagement of the coil in the tissue, slight counterclockwise co-rotation would not be expected to disengage the coil from the tissue. Lateral movement of the coil-rod, which has engaged the tissue of the arytenoid process, drags the process and the attached vocal process in a lateral direction, thus completing the desired function.

The manipulation of the described components is assisted preferably by use of a two-ended screw driver-type tool which selectively rotates the coil-rod assembly or the translation bushing. To that end, both components advantageously have slots 28, 30, respectively, to accommodate the respective blade or blades of the screw driver (not shown).

The anchor flange component 18 is generally cylindrical having a diameter of approximately 0.234"–0.250" at its distal end 31 and features a flange section 32 which serves to seat the component against the thyroid process. Internally, a threaded section 34 allows for the translation bushing to first be engaged, and later unthreaded, resulting in the desired axially movement of the coil-rod assembly 20.

The translation bushing 16 is approximately 0.200" in outer diameter at its widest section 35 and features an external thread 36 for threaded engagement with the internal threaded section 34 of the anchor component. A bore 38 is defined centrally through the translation bushing for axially accepting the coil-rod assembly 20.

In the illustrated embodiment, as noted above, the bushing has a radially inwardly directed flange 22 to define a reduced diameter bore segment 24. The reduced diameter bore segment has a diameter great enough to receive the coil 14 or other grasping device but less than the maximum diameter of the portion of the rod 10 inserted through the bushing bore 38 proximal end. This flange 22 limits the axial position of the rod 10 relative to the bushing. It is to be understood that the provision of a flange for engaging a distal end face of the rod is intended to be exemplary but not limiting. Indeed, other means for providing a shoulder respectively in the bushing bore and on the rod, for limiting displacement of the rod distally relative to the bushing, suitable for use in the environment of this invention, could be used and such suitable structures would be apparent to those of skill in the art.

As an alternative to providing a translation bushing as described above, a fly wheel type device 50 could be employed, axially constrained but freely rotatable relative to the anchor flange and threaded as at 52 to the coil-rod so that rotation thereof will displace the coil-rod laterally, axially relative to the anchor flange.

The coil-rod assembly features a rod 10 which is approximately 0.125" in diameter, and has a coil 14 mounted thereto to project axially, distally therefrom. The coil features a wire having a diameter of about 0.020" which is formed into a coil having a diameter of approximately 0.094". These dimensions, like all dimensions disclosed herein, are exemplary and define the currently preferred embodiment, but are not necessarily limiting of the invention. The coil features a sharp end which falls along the helix of the coil and allows for easy engagement into the tissue. In the illustrated embodiment, the coil form is created in a left-hand spiral which dictates the counterclockwise rotation for tissue engagement. The counterclockwise engagement rotation is significant when coupled with the counterclockwise rotation of the translation bushing since tissue engagement is maintained even if the coil-rod assembly inadvertently rotates when the bushing is rotated to lateralize the vocal cord. Indeed, clockwise engagement rotation might cause disengagement from the tissue when the bushing is rotated.

The coil component which engages the arytenoid tissue is significant in design function since it firmly engages the tissue without damaging it, and, if necessary, the coil can be removed by rotating the assembly in the clockwise direction. Exemplary alternate design configurations for the grasping device include hook components which serve to pierce the tissue. The hook design may be less desirable than the coil, however, since removal of such a component may be difficult. Pinching mechanisms may also be an alternative, but again may be less desirable because of possible damage to tissue. In addition, such mechanisms would be more costly to manufacture than the currently preferred coil structure.

The recommended surgical technique is supported with the use of a number of instruments which have been identified but not finalized. Thus, the description of such instruments is intended to be illustrative of the currently preferred embodiment, but not limiting.

To create the cavity for the anchor flange, a hand drill of diameter 0.234" is proposed. The dimensional (diametrical) mismatch between the drill and the anchor flange results in a "press-fit" condition which serves to lock the flange in place. The cavity described may also be created by using a hollow "crown" drill or potentially a spring loaded crown drill. Optimization of the drill and the recommended mode of driving (hand vs. powered drill) has not yet been determined. A holding forceps may also be introduced to eliminate any potential of the flange from rotating within the thyroid process.

Following the preparation of the cavity, the anchor flange is pressed into place. The anchor flange already has the translation bushing pre-threaded completely into place. The coil-rod assembly is introduced through the bore of the translation bushing, first by hand, and then rotated with the use of, for example, the screw driver blade. The coil-rod assembly is rotated counterclockwise until purchase of the tissue is achieved.

As an alternative to a coil, as described above, other tissue grasping configurations could be employed. In view of potential deficiencies of other grasping devices, however, the coil is currently anticipated to be easiest to use and most effective with minimal perceived damage to the related tissues.

The translation bushing is then unthread by using, for example, the opposite end of the dual blade screw driver, which engages the slots in the bushing but not the rod. The configuration of the screwdriver, other than to engage respectively the translation bushing and the coil-rod is not critical and one skilled in this art will readily appreciate from the foregoing suitable configurations for such a tool.

As can be seen in FIG. 1, the internal bore of the anchor flange has an enlarged diameter portion and a reduced diameter portion. The reduced diameter portion is threaded for engagement by the translation bushing. The shoulder 40 defined by the transition between the large diameter portion and the small diameter portion limits displacement of the translation bushing distally relative to the anchor flange by contacting a corresponding shoulder 42 of the translation bushing. As an alternative, the anchor flange can be of constant bore diameter and the translation bushing may be a two diameter structure so that abutment of the enlarged diameter portion of the translation bushing with the proximal end face of the anchor flange limits displacement of the former relative to the latter. In the event the enlarged diameter portion of the translation bushing remains proximal to the anchor flange, as an alternative to the use of a screw driver, the outer surface of the proximal end of the bushing may be provided with one or more pairs of diametrically opposed faces, for example a hexagon shape, for engagement with a wrench.

The counterclockwise rotation of the bushing, and the lack, in the illustrated embodiment, of a mechanical engagement between the bushing and the rod, allows for the bushing to be rotated independently of the coil-rod assembly. However, abutting engagement of the flange or otherwise defined radial shoulder of the bushing and the distal end face or otherwise defined radial shoulder of the rod displaces the coil-rod assembly, and the tissue engaged thereby, laterally. A holding forceps may also be introduced to ensure the independent rotation between the bushing and the rod or a suitable screwdriver may be used. Lab trials have shown that, periodically, the two components can catch and rotate in tandem. Although the device continues to function, the resultant movement of the tissue is suboptimal. As noted above, the counterclockwise rotation of the coil-rod required for tissue engagement does assure continued tissue contact. However, independent rotation is highly desirable.

Based on the efforts in the lab, the ability for the surgeon to trim the coil to a desired length has been considered desirable. To preserve the sharp tip, such length adjustment should desirably be achieved at the proximal end of the coil. For example, the coil can be adjusted in length by trimming the proximal extent of the coil and then securing the trimmed end of the coil in a known manner to the rod distal end. The option of choosing variable length coils or providing a variety of coil-rod assemblies is another option.

The foregoing description was directed in particular to lateralization of the vocal process. However, as would be apparent to the skilled artisan, the concept of the invention can be adapted to provide medialization of the vocal process. For example, to provide medialization of the vocal process, a multi-component structure that is generally similar to the above-described structure could be used. More particularly, the above-described rotational bushing is designed to direct the coil-rod assembly toward the targeted process where engagement and subsequent lateralization will occur. For medialization, the rotation bushing would be modified, for example to have a radiused nose which would serve to push (medialize) the process and/or engage a push-plate, suitably secured or implanted, as described below, which would medialize the process.

The rotational bushing required for the medialization will be very similar in size to the lateralization bushing but does not require a central bore or cannulation since the coil-rod assembly need not be provided. A push-plate, which would preferably be formed from UHMWPE, may or may not be required to medialize the process. It is contemplated that the push-plate, if required, would be inserted initially behind the thyroid cartilage, against the arytenoid cartilage. The anchor flange would then be inserted in a manner as described above. The medialization bushing would then be threaded into the flange, for example in a clockwise direction. As threading continues, the bushing will engage the push-plate, if provided, and medialize the process.

While the invention has been described in connection with what is presently considered to be the most practical and preferred embodiment, it is to be understood that the invention is not to be limited to the disclosed embodiment, but on the contrary is intended to cover various modifications and equivalent arrangements included within the spirit and scope of the appended claims.

What is claimed:

1. A method of improving a patient's airway while voice is minimally impaired, comprising:

providing an anchor component having a bore defined therethrough;

forming an aperture in a thyroid cartilage of a patient at substantially a vertical level of a vocal cord and an arytenoid cartilage;

inserting the anchor component through the aperture formed in the thyroid cartilage;

providing a lateralization/medialization assembly including a displaceable component having a tissue grasping device defined at a distal end thereof;

inserting said assembly into the bore of the anchor component;

grasping tissue including at least one of said arytenoid cartilage and tissue in a region thereof with said tissue grasping device; and displacing said displaceable component relative to said anchor component so as to displace said grasped tissue, thereby improving the patient's airway while voice is minimally impaired.

2. A method of improving a patient's airway while voice is minimally impaired, comprising:

providing an anchor component having a bore defined therethrough;

forming an aperture in a thyroid cartilage of a patient at substantially a vertical level of a vocal cord and an arytenoid cartilage;

inserting the anchor component through the aperture formed in the thyroid cartilage;

providing a lateralization/medialization assembly including a displaceable component having a tissue engaging device defined at a distal end thereof;

inserting said assembly into the bore of the anchor component;

operatively engaging said tissue engaging device with tissue comprising at least one of said arytenoid cartilage and tissue in a region thereof; and displacing said displaceable component relative to said anchor component so as to displace said operatively engaged tissue, thereby improving the patient's airway while voice is minimally impaired, wherein said step of providing an assembly comprises providing a translation component having a bore defined therethrough; and wherein said step of inserting said assembly into the anchor component comprises mounting said translation component to said anchor component and inserting said displaceable component through said bore of said translation component.

3. A method as claimed in claim 2, wherein said step of inserting said displaceable component through said bore of said translation component follows said step of mounting said translation component to said anchor component, wherein said translation component comprises a translation bushing, and wherein displacement of said translation bushing relative to said anchor component displaces said displaceable component axially relative to said anchor component, and wherein said step of displacing said assembly relative to said anchor component comprises displacing said translation bushing relative to said anchor.

4. A method as claimed in claim 3, wherein said step of mounting said translation bushing comprises threading said translation bushing into said anchor.

5. A method as claimed in claim 4, wherein said step of displacing said translation bushing comprises unthreading said translation bushing.

6. A method as claimed in claim 1, wherein said tissue grasping device comprises a coil and wherein said step of grasping comprises rotating said tissue grasping device so as to screw said coil into at least one of the arytenoid cartilage and tissue in the region thereof.

7. A method as claimed in claim 6, wherein said coil is formed as a left-handed spiral and wherein said step of rotating comprises rotating said tissue grasping device counter-clockwise.

8. A method as claimed in claim 1, wherein said step of providing an anchor component comprises providing an anchor component of generally tubular configuration, having a generally circular cross-section and a generally cylindrical bore defined therethrough.

9. A method as claimed in claim 1, wherein said step of providing an anchor component comprises providing an anchor component having a flange projecting generally radially outwardly from an outer peripheral surface thereof.

10. A method as claimed in claim 1, wherein said step of providing an assembly comprises providing a assembly including a rod of generally circular cross-section.

11. A device for lateralization and/or medialization of a vocal cord of a patient, comprising:

an anchor component having a bore defined therethrough;

a lateralization/medialization assembly including a displaceable component having a tissue grasping device defined at a distal end thereof for selectively grasping tissue including at least one of an arytenoid cartilage of a patient and tissue in a region thereof;

said assembly being received in the bore of the anchor component;

said displaceable component being selectively displaceable relative to said anchor component so as to selectively displace the grasped tissue to at least one of lateralize and medialize a vocal cord of the patient to improve an airway of the patient while voice is minimally impaired.

12. A device for lateralization and/or medialization of a vocal cord of a patient, comprising:

an anchor component having a bore defined therethrough;

a lateralization/medialization assembly including a displaceable component having a tissue engaging device defined at a distal end thereof for selectively engaging at least one of an arytenoid cartilage of a patient and tissue in a region thereof;

said assembly being received in the bore of the anchor component;

means for displacing said displaceable component relative to said anchor component so as to selectively lateralize and or medialize a vocal cord of the patient to improve an airway of the patient while voice is minimally impaired, wherein said assembly comprises a translation component having a bore defined therethrough, said translation component being mounted to said anchor component, said displaceable component being inserted through said bore of said translation component.

13. A device as claimed in claim 12, wherein said translation component comprises a translation bushing that is operatively coupled to said displaceable component so that displacement of said translation bushing relative to said anchor component displaces said displaceable component axially relative to said anchor component, thereby providing said means for displacing.

14. A device as claimed in claim 13, wherein said translation bushing is threaded into said anchor and wherein said translation bushing is operatively coupled to said displaceable component so that when said translation bushing is unthreaded relative to said anchor component, said displaceable component is displaced axially relative to said anchor component.

15. A device as claimed in claim 11, wherein said tissue grasping device comprises a coil.

16. A device as claimed in claim 15, wherein said coil is formed as a left-handed spiral.

17. A device as claimed in claim 11, wherein said anchor component has a generally tubular configuration, having a generally circular cross-section and a generally cylindrical bore defined therethrough.

18. A device as claimed in claim 11, wherein said anchor component has a flange projecting generally radially outwardly from an outer peripheral surface thereof.

19. A device as claimed in claim 11, wherein said displaceable component comprises a rod having a generally circular cross-section.

20. A device as claimed in claim 13, wherein said translation bushing includes means defining a radial shoulder in said bore thereof for abutting a radial shoulder defined on said displaceable component when said translation bushing is displaced axially relative to said anchor component.

21. A device for lateralization and/or medialization of a vocal cord of a patient, comprising:

an anchor component having a bore defined therethrough;

a lateralization/medialization assembly including a displaceable component having a tissue engaging device defined at a distal end thereof for selectively engaging at least one of an arytenoid cartilage of a patient and tissue in a region thereof;

said assembly being received in the bore of the anchor component;

means for displacing said displaceable component relative to said anchor component so as to selectively lateralize and or medialize a vocal cord of the patient to improve an airway of the patient while voice is minimally impaired, wherein said means for displacing comprises a translation component, said translation component being mounted to said anchor component, said displaceable component being operatively engaged with said translation component so that rotation of said translation component relative to said anchor component displaces said displaceable component axially along a longitudinal axis of said anchor component.

22. A device as in claim 21, wherein said translation component has a bore defined therethrough, said displaceable component being inserted through said bore of said translation component.

* * * * *